United States Patent [19]

Hannotiau et al.

[11] Patent Number: 5,396,080
[45] Date of Patent: Mar. 7, 1995

[54] THIN FILM THICKNESS MONITORING WITH THE INTENSITY OF REFLECTED LIGHT MEASURED AT AT LEAST TWO DISCRETE MONITORING WAVELENGTHS

[75] Inventors: Michel Hannotiau, Jodoigne; Guy Renard, Tarcienne; Robert Terneu, Thiméon, all of Belgium

[73] Assignee: Glaverbel, Brussels, Belgium

[21] Appl. No.: 120,359

[22] Filed: Sep. 14, 1993

[30] Foreign Application Priority Data

Sep. 15, 1992 [GB] United Kingdom ............... 9219450

[51] Int. Cl.⁶ .......................................... G01N 21/86
[52] U.S. Cl. .................................... 250/560; 356/381
[58] Field of Search .............. 250/560, 565, 571, 574; 356/432, 435, 355, 381, 394

[56] References Cited

U.S. PATENT DOCUMENTS

| | | |
|---|---|---|
| 3,892,490 | 7/1975 | Uetsuki et al. . |
| 4,743,775 | 5/1988 | Edgar .................................. 250/560 |
| 4,748,329 | 5/1988 | Cielo et al. . |
| 4,957,370 | 9/1990 | Tominaga et al. . |
| 4,977,330 | 12/1990 | Batchelder et al. . |
| 5,101,111 | 3/1992 | Kondo .................................. 250/560 |

FOREIGN PATENT DOCUMENTS

| | | |
|---|---|---|
| 0169664 | 1/1986 | European Pat. Off. . |
| 58-030605 | 2/1983 | Japan . |
| 2016678A | 9/1979 | United Kingdom . |
| 2069130A | 8/1981 | United Kingdom . |

Primary Examiner—David C. Nelms
Assistant Examiner—Que T. Le
Attorney, Agent, or Firm—Spencer, Frank & Schneider

[57] ABSTRACT

A method is described for monitoring the thickness and uniformity of a transparent coating applied to a substrate in sheet form. The method comprises directing polychromatic light at the coating at a plurality of locations and measuring the intensity of light reflected from said coating. At each location, the intensity of reflected light is measured at at least two discrete monitoring wavelengths and said measurements are processed to generate an electrical signal which may be compared with one or more predetermined threshold values and with such electrical signals generated at other locations to yield indications of whether the thickness and uniformity of the coating lies within predetermined tolerance values.. The first discrete monitoring wavelength lies in the range 400 to 480 nm (blue) and the second discrete monitoring wavelength lies in the range 580 to 750 nm (red). A third discrete monitoring wavelength, which lies in the range 480 to 580 nm (green) may also be used. The monitoring results may be used to adjust the coating process.

32 Claims, 5 Drawing Sheets

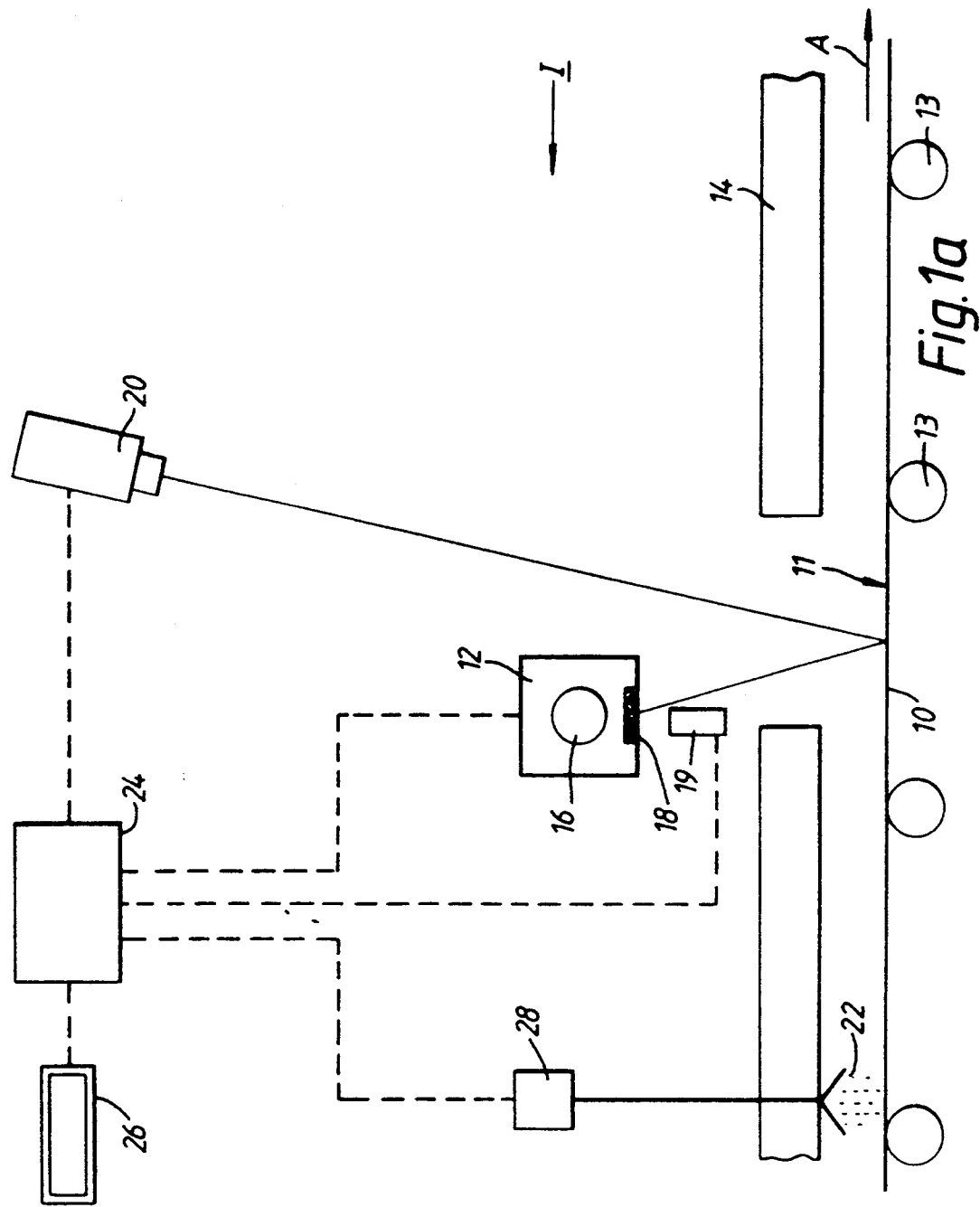

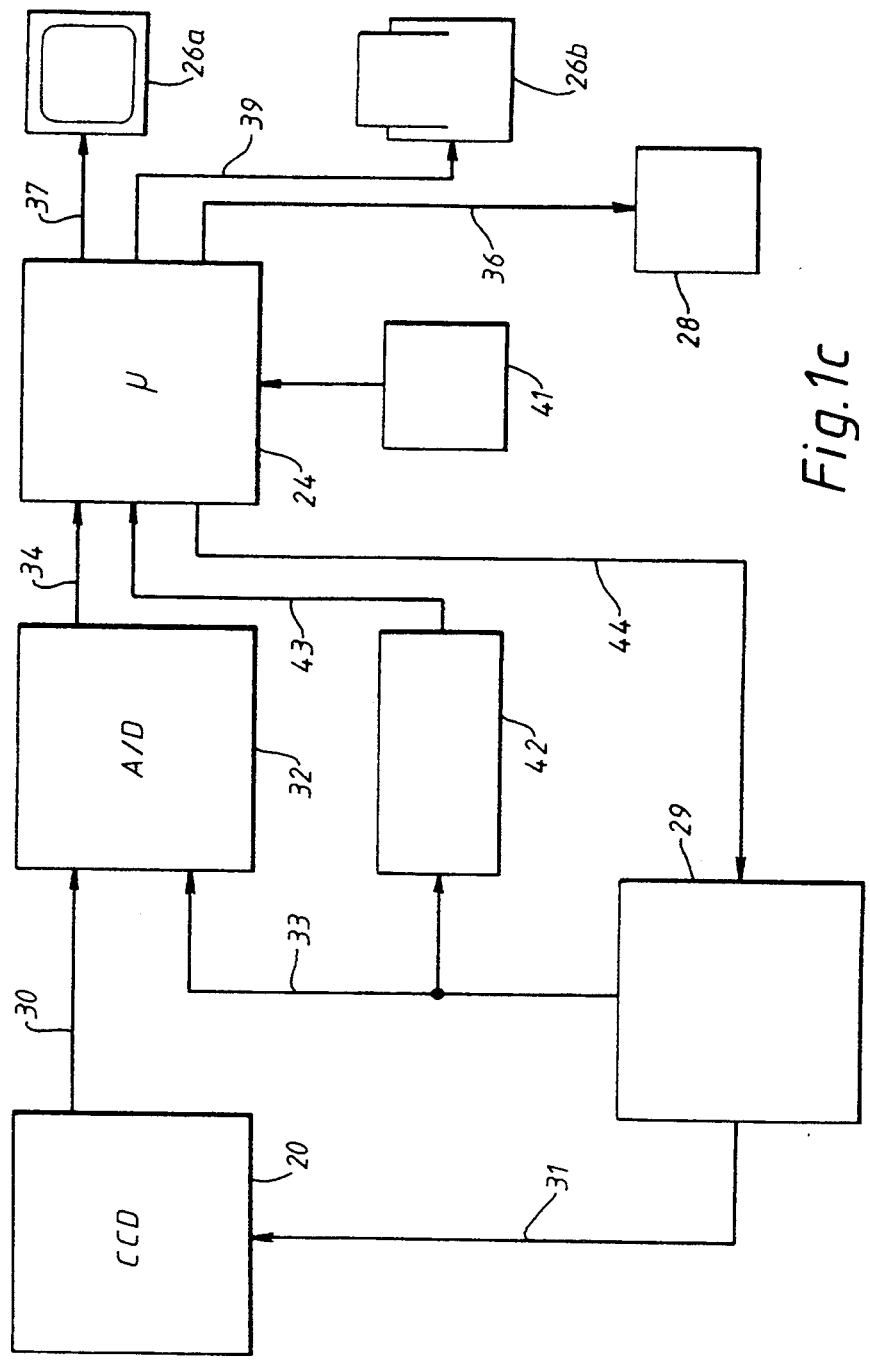

THIN FILM THICKNESS MONITORING WITH THE INTENSITY OF REFLECTED LIGHT MEASURED AT AT LEAST TWO DISCRETE MONITORING WAVELENGTHS

BACKGROUND OF THE INVENTION

1. Field of the Invention

This invention relates to a process for the monitoring of thin films on a substrate, particularly for the monitoring of a transparent coating applied to a substrate, such as coatings on glass.

Control of the thickness, and also the refractive index, of coatings applied to glass sheets, especially freshly formed ribbons of glass, is important. As is well known in the art, one or more coatings are applied to glass sheets for a number of purposes. These coatings are often thin, for example less than 100 nm, and the measurement of films of this thickness presents difficulties, especially where it is desired to make rapid and continuous measurements over large areas of glass and to detect variations in thickness both along and across the glass ribbon or sheets.

The thickness of these coatings is a very important element in the control of quality of glazing formed from coated glass sheets. The physical and optical properties of the glazing depend strongly on the thickness of the coating. The geometric thickness and the refractive index of the coating play a predominant role in the interference properties of the coated sheet.

If one establishes that the measured value of the thickness of a sample is outside the allowed tolerances, the sheets of glass which have been coated in the meantime will be wasted. This is a particular problem if in the meantime the coated sheets have already been subjected to a further coating or have been made up into glazing panels.

It is therefore desirable to monitor the thickness of the coating as quickly as possible after the deposit of the coating in the industrial production line.

2. Description of the Related Art

British patent Specification GB 2069130 (RCA) describes a method for monitoring the optical thickness of a coating by directing polychromatic light at the sample and successively at a control sample with a coating of known thickness and varying the thickness of the comparison coating until the reflected spectra correspond. This method is suitable for coating optical thicknesses of 150 nm to 3000 nm. The method also requires accurate calibration of the comparison coating.

The process described in GB 2069130 does not permit the control of geometric thicknesses thinner than about 75 nm (given a coating refractive index approaching 2). In addition, the described process is not concerned with the continuous control of coating thicknesses where the measured values fall outside threshold values, nor is it possible with the described apparatus to monitor the uniformity of thickness of the coating. Furthermore, the positioning of the apparatus described in GB 2 069 130 immediately following coating, is difficult.

SUMMARY OF THE INVENTION

According to the invention there is provided a method of monitoring the thickness and uniformity of thickness of a transparent coating applied to a substrate in sheet form, comprising directing polychromatic light at the coating at a plurality of locations and measuring the intensity of light reflected therefrom, wherein, at each location, the intensity of reflected light is measured at at least two discrete monitoring wavelengths and said measurements are processed to generate an electrical signal which may be compared with one or more predetermined threshold values and with such electrical signals generated at other locations to yield indications of whether the thickness of the coating lies within predetermined tolerance values.

The invention also provides an apparatus for monitoring the thickness and uniformity of thickness of a transparent coating applied to a substrate, comprising:

(i) a light source for directing polychromatic light at a plurality of locations on the coating;

(ii) means for measuring the; intensity of light reflected from said coating at each location at at least two discrete monitoring wavelengths; and (iii) means for processing the measurements to generate an electrical signal which may be compared with one or more predetermined threshold values and with such electrical signals generated at other locations to yield an indication of whether the thickness of the coating lies within predetermined tolerance values.

The process and apparatus according to the invention allow the easy monitoring of the thickness, uniformity of thickness and optionally the index of refraction of a coating within pre-defined tolerance values. The invention also allows, in a simple manner, this monitoring to take place rapidly after formation of the coating.

By "discrete" monitoring wavelengths we mean wavelengths that are separated from each other by at least 50 nm. The two discrete monitoring wavelengths preferably each lie within the., visible spectrum, that is within the range of 380 nm to 780 nm. The most preferred discrete monitoring wavelengths lie in the range 400 to 480 nm (blue) and in the range 580 to 750 nm (red). This is because of the discovery that, for many commercial coatings, the difference between the measurements taken at these two discrete monitoring wavelengths varies significantly with coating thickness.

The reflectivity of light from a coated substrate is known to depend inter alia upon the wavelength of reflected light the coating thickness and the refractive indices of the substrate, the coating and of air. It is complicated to derive all the necessary parameters to enable the coating thickness to be calculated directly from the measurement of reflectivity at two discrete monitoring wavelengths, in practice it is more convenient to determine tolerance values, for example from reflectivity measurements from samples carrying coatings of known thickness.

The output of the reflected light measurements are preferably fed to a micro-processor, where the signals are processed, as explained further below, to produce an indication of coating thickness. At certain wavelengths depending on the optical thickness of the coating, interference occurs resulting in a reflected spectrum characteristic of that optical thickness. For a given coating with a given thickness, a dominant wavelength usually exists within the visible spectrum at which constructive interference occurs and it is this dominant wavelength which determines the visual appearance of the coated substrate.

We have found that for small thicknesses and discrete monitoring wavelengths close to that of the dominant wavelength, the difference between the reflectivity at two wavelengths is proportional to the coating optical thickness and thus, where the refractive index of the coating is constant, to the geometric thickness of the coating.

However, the exact relationship between the reflectivities at various wavelengths is complicated. Rather than measure thickness in absolute terms therefore, the present invention includes the establishment of tolerance limits for each kind of coating. These tolerance limits are determined by trial.

When measurement at two discrete monitoring wavelengths is insufficient to provide an accurate indication of coating thickness, for example where the discrete monitoring wavelengths do not lie close to the dominant wavelength, the measurements should be taken at at least three wavelengths, the third discrete monitoring wavelength preferably being in the range 480 to 580 nm (green). From the three measurements taken, the most appropriate pair of measurements may then be selected to generate an indication of coating thickness. The average of the three measurements provides more precise information on luminous reflectivity, which can be used in some preferred embodiments as an indication of refractive index.

Where the variation of reflectivity with thickness lies close to a maximum, reflectivity varies very little with coating thickness, so that the reflectivity then depends more directly on the index of refraction, as predicted by the Fresnel equations. By means of proper calibration, one may thereby easily determine the refractive index of the coating.

Uniformity of the thickness, of the coating on the substrate is indicated by comparison between the electrical signal generated at one location on the coating and such signals generated at other locations. The relative spacing of these locations determines the reliability of the uniformity data which is so generated. Depending upon the desired quality of the coated substrate and its intended end use, we prefer to monitor the thickness of the coating at a plurality of locations which are spaced apart by not more than 200 mm, most preferably not more than 100 mm, such as locations spaced apart by not more than 50 mm, ideally not more than 10 mm, most ideally not more than 5 mm.

A suitable device for carrying out the monitoring would operate in a manner whereby the intensity of reflected light is measured by different light sensitive elements for each discrete monitoring wavelength. The photosensitive elements may be photosensitive diodes, for example arranged in a photo-diode array. A charge coupled device (CCD), in particular a linear colour CCD camera is used for preference. Alternatively at least two monochrome CCD linear cameras may be used, each fitted with an appropriate filter. The use of a colour camera which is sensitive to three wavelengths has the advantage however that the three signals are more easily comparable because they are obtained under the same conditions with the same apparatus. Further, when such a camera is sensitive to the "primary" colours blue, green and red the output signals from the camera are more truly a fair representation of how the coated substrate will appear to the human eye. The camera may be provided with an infra-red filter to prevent overheating if exposed to an environment at elevated temperature and, depending on the nature of the light source, a broad band filter to correct the white light balance.

The substrate is usually in the form of a rigid transparent sheet. The index of refraction of the substrate may be smaller or greater than that of the coating. The substrate is usually a vitreous material such as glass, having a refractive index of typically 1.52 (soda-glass) but the method of the present invention is equally applicable to the monitoring of coating thicknesses on other such substrate material, such as plastic material.

The coating may be applied to the substrate by a variety of methods including cathodic sputtering under vacuum (carried out at ambient temperatures), pyrolysis (carried out at elevated temperatures) and CVD (chemical vapour deposition). Various coating materials are used in the art for a variety of purposes. Coating materials are usually selected from metals, metal oxides, metal nitrides and mixtures thereof. Examples of coating materials include metals such as silver and silicon, oxides such as alumina (refractive index about 1.7), tin oxide (refractive index about 1.9 when deposited by pyrolysis), zirconium oxide (refractive index about 2.0 when deposited by CVD) and silica (refractive index about 1.4 when deposited by CVD) and nitrides such as titanium nitride, silicon nitride and aluminium nitride. Luminous transmission should be non-diffuse and is preferably at least 10%, most preferably at least 20%.

The source of polychromatic light may simply be a source of the two or more wavelengths for which measurements are to be made but it is more convenient simply to use a source of white light. Preferably, the measurements are taken over substantially the whole width of the substrate. Ideally therefore, the light source is an elongate light source having a length equal to at least the width of the coating.

The arrangement may be positioned above a moving coated glass ribbon, and comprise directing the light in the form of a slit from an elongate light source positioned across the width of the coated glass ribbon as the latter passes. The light source may comprise TL fluorescent tubes. Preferably, the illumination from the light source, that is the intensity of the polychromatic light directed at the coating, is controlled and the means for achieving such control may include at least one photodetector. With the aid of photodetectors, the light source may be calibrated by measuring the illumination at a number of selected points distributed over the width of the substrate (for example at a dozen of points distributed over the width of a ribbon of glass which is typically 3.2 m wide). The measured illumination levels are stored. During the coating process, the illumination at the selected points is measured. If a variation from the stored values occurs, a correction proportional to the variation may automatically be applied to compensate therefor.

An alternative light source less sensitive to temperature may be used in place of the fluorescent tubes, such as light projectors, for example spot lamps.

For example, with a light source consisting of three light projectors, three photodetectors would be sufficient for this control.

To provide more uniform illumination, a frosted glass filter may be interposed between the light source and the coating.

For on line coating on a conveyor, the measurements of the intensity of reflected light should be taken immediately following the coating step, near the downstream end of the glass coating station.

Calibration of the camera may be achieved by measuring the reflection from an un-coated substrate and setting the indication of coating thickness to zero.

With an adapted calibration and threshold values predetermined, we have found that the invention permits the easy monitoring of the thickness and uniformity of the coating during the course of manufacture. The method may give information in real time, immediately following the deposit of the coating. If one defines the limits beforehand, an alarm may function when these limits have been exceeded and/or a reaction loop may be triggered to adjust the coating conditions to correct the fault.

The threshold values may usefully be obtained by measuring the intensity of reflected light from samples having known coating thickness, at the extremes of the desired manufacturing tolerances.

Thus, according to a preferred embodiment of the invention, there is provided a method for applying a transparent coating to a substrate in sheet form, comprising the steps of:

(a) applying coating material to the substrate;

(b) monitoring the thickness and uniformity of the thickness of the coating by directing polychromatic light at a plurality of locations on the coating, measuring the intensity of light reflected therefrom at each said location at at least two discrete monitoring wavelengths and processing said measurements to generate an electrical signal which is compared with one or more predetermined threshold values and with such electrical signals generated at other locations to yield an indication of whether the thickness of the coating lies within predetermined tolerance values; and (c) adjusting the coating parameters in response to said electrical signal, if necessary.

Given that it is difficult to measure the thickness of thin coatings it is surprising that one may be able to monitor the thickness during the course of manufacture, without disturbing the manufacture by the simple analysis of 2 electrical signals derived at different wavelengths, and particularly in the hot environment immediately following a coating process.

Where a substrate is provided with two or more thin coatings thereon, deposited in sequence, it is possible to perform the method of the present invention immediately after each coating step and/or after all the coatings have been deposited.

It is also possible to carry out sampling of a coated substrate at regular intervals during manufacture thereof and to inspect these samples by the method according to the invention outside the production line, for example in a laboratory.

The invention is particularly, useful where the measurements are made on a moving substrate, such as for example where the substrate is glass and the measurements am made on a moving glass ribbon or moving glass sheets at a location along the production line for the continuous production of coated glass sheets, such as in a cathode vacuum sputtering apparatus or within the annealing lehr on a ribbon of glass obtained by the "float" process. This method is particularly applicable to coatings formed by pyrolysis, the measurements may be taken when the glass is at about 150° C. The measurements are preferably taken within 20 m from the downstream end of the glass-coating station. For example, measurements may be taken when the glass is at about 500° C. to 600° C. The light source and the camera are preferably mounted above the vault wall of the annealing lehr, a slot in the vault wall enabling exposure of the ribbon of glass to the light source and the camera. To further protect the light source and the camera from heat escaping from the annealing lehr, including through the slot in the vault wall thereof, the light source and/or the camera may be enclosed within a refrigerated space, cooled for example by static cold air, by a current of air or by water.

The adjustment of the application of coating material to the substrate in response to the electrical signal may be achieved by a variety of methods according to the coating process being used, for example, by changing the rate of delivery of the coating material at the coating station, by changing the speed of the moving spray head and/or by changing the environmental conditions, such as temperature, in the .coating station so as to influence the coating process in the desired manner.

While as described above, the method according to the invention may include the additional step of adjusting the coating parameters in response to said electrical signal, this is not essential. It is also possible to use the electrical signal for sorting coated substrate samples into batches of different quality, destined for example for different end uses. Further, the electrical signal may be used for determining the nature of subsequent processing of the coated substrate.

BRIEF DESCRIPTION OF THE DRAWINGS

The invention will now be described in further detail, purely by way of example, with reference to the accompanying drawings, in which:

FIG. 1A shows schematically an arrangement, viewed from one side, of an apparatus suitable for carrying out a method according to the invention;

FIG. 1B is a view taken in the direction "I" in FIG. 1a;

FIG. 1C shows schematically a circuit arrangement suitable for use with the apparatus shown in FIGS. 1a and 1b;

DESCRIPTION OF THE PREFERRED EMBODIMENTS

Figure 1B:
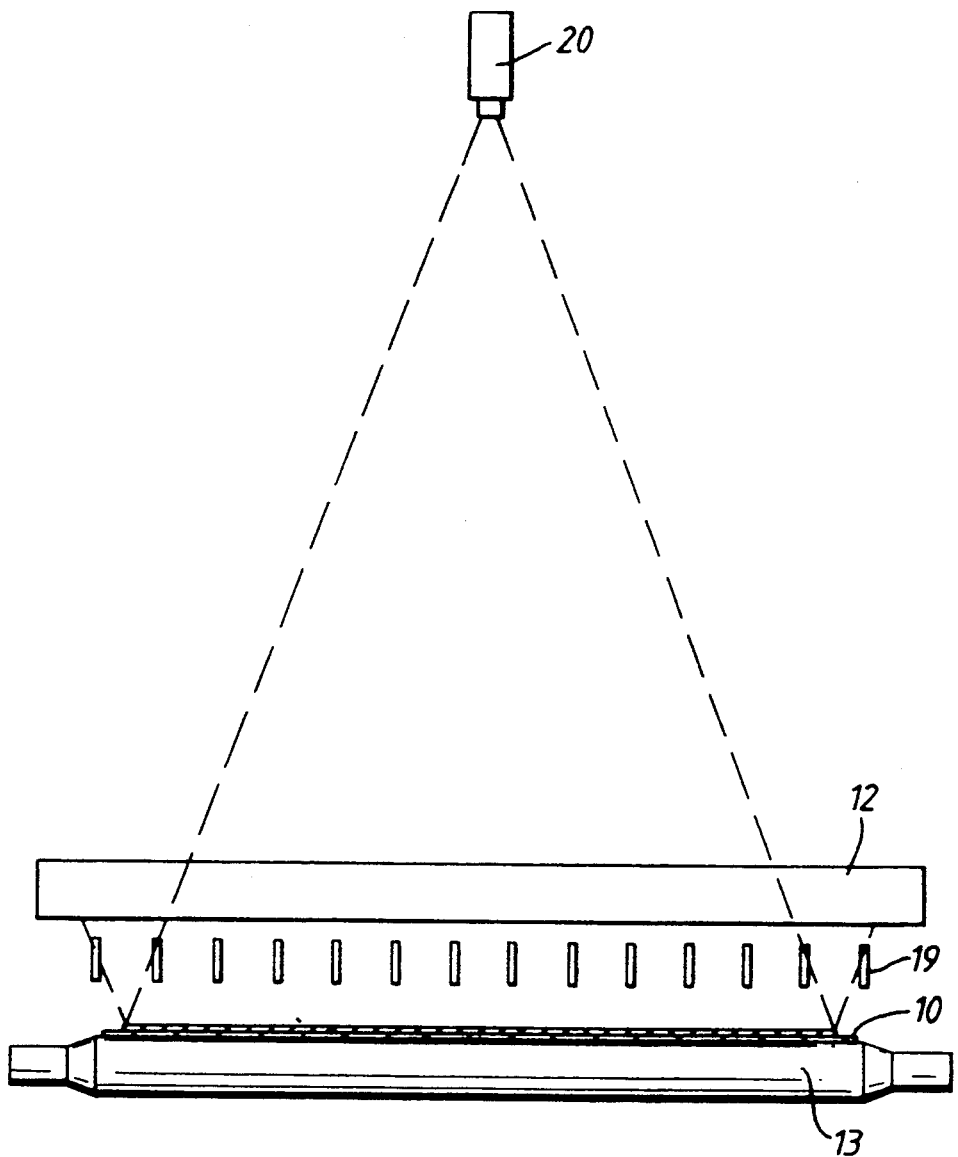

Referring to FIGS. 1A, 1B and 1C, positioned in an annealing lehr immediately following the application of the coating to a ribbon of glass 10, is a light box 12 extending across the lehr. The light box is spaced for example about 50 cm above the vault wall 14, that is about 1 m above the glass ribbon 10. The glass ribbon 10 is supported on transport rollers 13. A beam of light from the light box is incident on the upper coated surface 11 of the glass ribbon 10 at an angle close to being normal to that surface (exaggerated in FIG. 1A for clarity) and the reflected beam passes to a CCD linear colour camera 20 centrally positioned relative to the width of the ribbon, about 3 to 4 m above the glass ribbon 10. The light box 12 contains TL (fluorescent) tubes 16 driven by a 20,000 Hz supply. It is important to ensure that the luminosity of the light source is as uniform as possible along the length of the light box. To assist in this a frosted glass window 18 covers the light exit from the light box 12. As an alternative, the TL fluorescent tubes 16 may be replaced by three light projectors for illuminating the frosted glass window 18.

The illumination from the light box 12 may be controlled by means of 14 photodetectors 19 positioned at a number of selected points distributed over the width of the substrate across the width of the glass ribbon 10. The light source 12 may be calibrated by measuring the illumination therefrom at each of the photodetectors 19. The measured illumination levels are stored in the memory of a microprocessor 24. During the coating process, the illumination at the selected points is measured. If a variation from the stored values occurs, a correction proportional to the variation is automatically generated by the microprocessor 24 to be applied to the electrical signals provided by the pixels of the CCD camera 20 viewing the zone adjacent that photodetector 19 which has detected the variation. Where light projectors are used in place of the fluorescent tubes 16, the correction generated by the microprocessor may be applied directly to the light source 12.

The glass ribbon 10 moves in the direction of the arrow A, past a reciprocating spray head 22 of the coating station. Control means 28 adjust the flow rate of material through the spray head 22 and/or the reciprocating speed of the spray head. The measurements from the camera 20 pass to the micro-processor 24 where the necessary calculations are carried out as explained in more detail with reference to FIG. 1C. A display device 26 displays an indication of the thickness of the coating or whatever other parameters the micro-processor 24 may be programmed to calculate. A connection between the micro-processor 24 and the control means 28 enables automatic control of coating thickness.

A suitable camera is the TL-2600 RGB Colour Line Scan Camera from PULNIX. The camera is equipped with a 50 mm focal length objective and an infra-red filter to reduce the risk of heat damage to the camera. The width of the light beam from the light box 12 is wider than the width of the glass ribbon 10 to ensure that the camera receives reflected light from the whole width of the coated glass ribbon, account being taken of the spacing between the light box and the glass and between the glass and the camera objective.

The TL-2600 RGB Colour Line Scan camera 20 is constituted by 3 lines of 864 active pixels, which for a ribbon width of about 3.2 m gives a resolution of about 4 mm, a sufficiently high resolution for the present purposes. Each pixel is a microscopic photodetector with a size of $14 \times 14$ μm. An optical pass-band filter is positioned in front of each of the three lines of pixels, corresponding respectively to the red, green and blue wavelengths. An infra-red cut-off filter and 2 optical pass-band filters are placed in front of the objective of the camera 20, the response curves of which allow for equilibration adjustment of the level of illumination at the red, green and blue wavelengths.

Referring in particular to FIG. 1C, the integration time of the electrical charges which accumulate on each pixel are adjustable. The sensitivity of capture for each type of coating may thereby be adjusted, to take account of the fact that there is a significant difference in the level of light falling on the camera 20 between a layer which reflects 1.0% of the light and a layer which reflects 50% of the light. This adjustment determines the level of the signals which are output from the camera 20 on line 30. The camera 20 is fed with a synchronising pulse from the clock signal generator 29 along line 31, which pulse triggers the transfer of charge from each pixel to the neighbouring pixel. The integration time must be larger than the number of pixels of the camera 20 multiplied by the time T separating 2 synchronising pulses. In the present case, in order to take account of "black" pixels, the integration time is greater than $2700 \times T$.

The electrical signals produced by the camera represent the reflectivity of the coated surface to the three colours red, green and blue (respectively approximately 580–700 nm, 515 nm and 420–450 nm). These signals, designated herein as "[R]", "[G]" and "[B]", are passed to the micro-processor 24 where they are used to deduce the thickness and optionally the refractive index of the coating.

The analogue electrical signals, [R], [G] and [B], resulting from the three lines of pixels, having amplitudes proportional to the quantity of light captured by each pixel, are multiplexed by pixel firstly, the [R], [G] and [B] signals for the first pixel of each of the three lines, then the same for the second pixel of each of the three lines and so on. These multiplexed signals are sent towards an 8-bit analogue-to-digital converter 32, which is also fed with a synchronising pulse from the clock signal generator 29 along line 33. The synchronising pulse from the clock signal generator 29 is also fed to a colour identification signal generator 42. The digital signals output from the analogue-to-digital converter 32 are then sent via line 34, simultaneously with a 3-bit colour identification signal from the signal generator 42 via line 43 to a microprocessor 24 for data treatment.

The micro-processor 24 effects a treatment of the signal and manages the parameters of the system. The calculations are made pixel by pixel for each colour. The resulting values allow the plotting of graphs.

The micro-processor 24 calculates the average of the signals [R], [G] and [B], i.e. ([R]+[G]+[B])/3 to indicate the refelectivity of the coating. The micro-processor 24 also calculates the difference between two signals to indicate the thickness of the coating at a constant refractive index, i.e. [R]−[B], [R]−[G], or [G]−[B].

It is also possible for the micro-processor 24 to smooth out the [R], [G] and [B] curves, i.e. to establish, if desired, "smoothed" curves of reflection at each of the [R], [G] and [B] wavelengths by calculating the average of a certain, adjustable, number of pixels of the same colour, such as 3 or 5 adjacent pixels. This reduces, if desired, differences of local signal values between one pixel and its neighbour, due for example to movements of the hot air in the gallery which change the illumination conditions of the layer, or clue to dust etc.

If desired, the micro-processor 24 may be programmed to generate a reaction loop command signal, fed to line 36, to the control means 28, to adjust the parameters of the coating deposition process.

It is also possible to calculate and to apply correction coefficients to each [R], [G] and [B] signal, in order that they correspond to the normalised colorimetric values (trichromatic CIE co-ordinates or Hunter co-ordinates L,a,b). In this case, there will also be need to take account of the substrate (clear glass, bronze glass, grey glass etc.) and its thickness. In this case, the measurement will no longer be relative, but absolute.

To display the treated data signals in graphical form, the treated signals from the micro-processor 24 may be fed via a line 37 to a video screen 26a and/or via a line 39 to a printer or plotter 26b.

Upper and lower limits corresponding to acceptable manufacturing tolerances are determined by taking measurements on reference control samples themselves controlled by laboratory apparatus. These limits may also be displayed on the video screen 26a and/or on the printed graph from the printer or plotter 26b, for example in the form of two horizontal straight dotted lines. This allows the operator to easily see if the thickness (and the refractive index if this data is included) exceed the tolerance limits and to which regions of the width of the glass substrate these excesses are derived.

Calibration of the apparatus is achieved by measuring the reflection from an un-coated glass ribbon, enabling the indication of coating thickness to be set to zero. Any non-uniformity of illumination over the width of the ribbon of glass, any errors due to imperfections in the camera optics and any differences in the sensitivity of the pixels of the camera 20, are compensated for by reference to the glass before the application of the coating. This calibration leads to the application of correction coefficients to the values of the signals of each pixel in order to obtain 3 flat response curves. This calibration can be carried out immediately prior to the deposition of the coating being started, and should be effected before each run of depositing the coating.

The calibration coefficients are, for example, determined such that the output signals with un-coated glass, after amplification, are all situated at the centre of the possible output range for the chosen camera 20, i.e. at 50% of maximum amplitude. This choice of 50% for un-coated glass may vary however as a function of the type of coating, i.e.. according to the level of luminous reflection.

For each of the pixels of each of the three colours, one can then store the coefficient to apply to the value of the signal that this pixel provides, so that this value corresponds to the chosen 50%. This coefficient is then applied to all subsequent signals from this pixel.

With the object to minimise the errors arising from an undulation of the ribbon over the transporter (reflections of the luminous source from different points which are not necessarily uniform) or from turbulence in the hot air in the interior of the annealing gallery (fluctuations in the refractive index of air in the interior of the gallery), a certain adjustable number of acquisitions of entire sets of values [R], [G] and [B] are considered and the average values corresponding to an advance of the glass are calculated.

Preferably an average of about 90 readings are taken corresponding to about 6 m length of glass ribbon. This average is compared with pre-set upper and lower limits enabling the operator to see if the tolerances are exceeded at any point across the width of the ribbon.

The entry of the function parameters (integration time, number of acquisitions of a given series of data before effecting an average, calibration coefficients etc.) and the choice of functions and the desired outputs, may be made with the aid of a keyboard 41 associated with the micro-processor 24.

The micro-processor 24 sends required camera command signals via line 44 to the clock signal generator 29, from where they are passed on to the camera 20 via line 31.

EXAMPLE 1

A solution containing aluminium compound is sprayed through a reciprocating spray-head onto a travelling ribbon of hot glass at a temperature of more than 550° C. The purpose of this alumina undercoat is that when an "overcoat" of tin oxide is applied, the optical thickness of the undercoat is sufficient to reduce the reflected visible light interference effects due to the overcoat. To achieve this objective the limits of the thickness of the alumina coating are very narrow. Depending on the thickness of the subsequently applied $SnO_2$ layer the alumina coating should have a thickness within the range of 75 to 100 nm with a tolerance of, for example, ±3 nm and an index of refraction of between 1.68 and 1.73±0.01.

Figure 2:
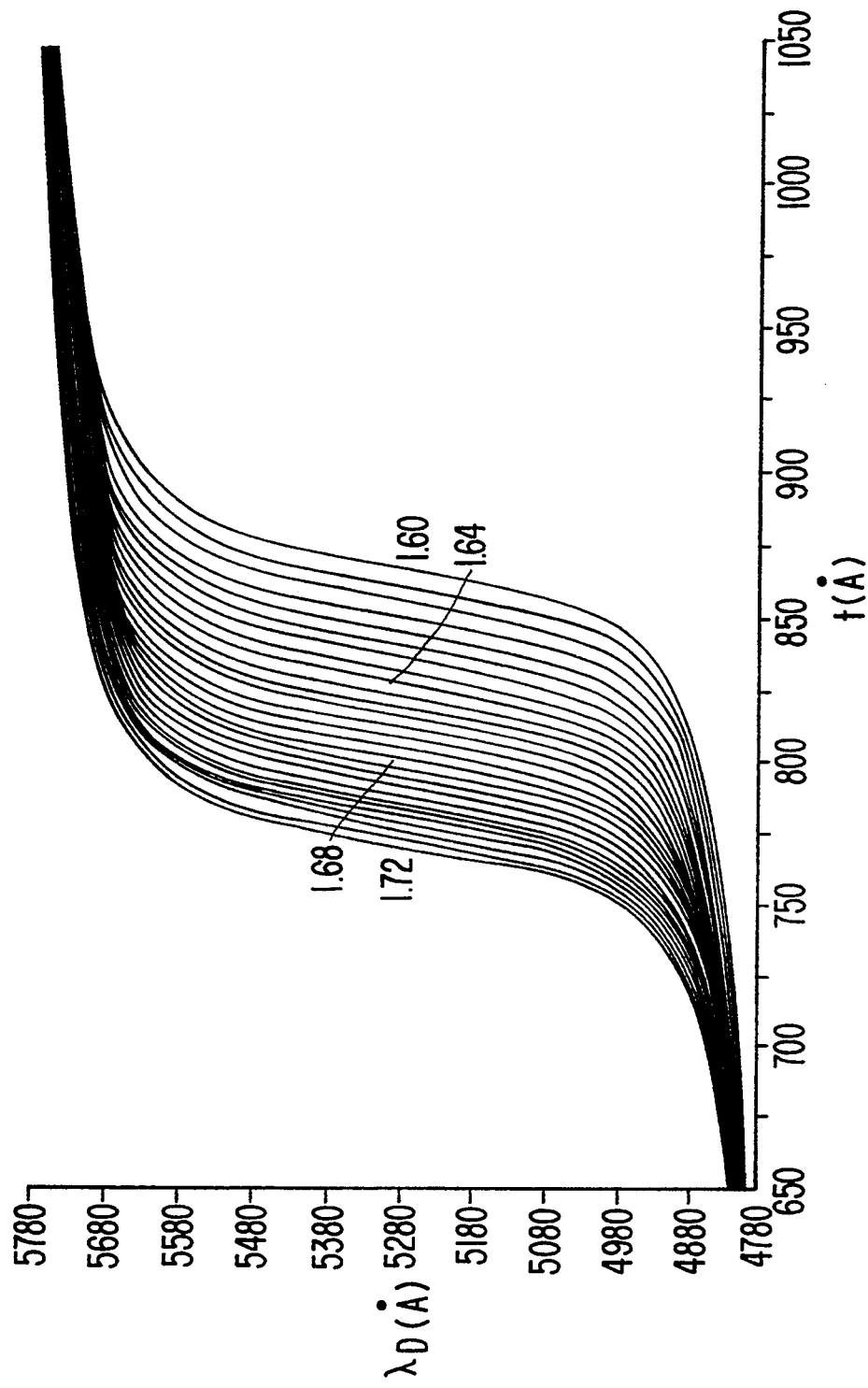
FIG. 2 shows the relationship between predominant reflected wavelength and coating thickness between 65 and 105 mm, for alumina coatings of various refractive indices.

For coatings of this intended thickness and refractive index the dominant reflected wavelength is within the range 480 nm to 575 mm, that is within the range of blue to yellow. As thickness increases, the reflected colour shifts from blue at a thickness of 75-80 nm to slightly yellow at a thickness of 100 mm. This is shown in FIG. 2 where the dominant reflected wavelength $\lambda_D$ is plotted against the coating thickness t, for coatings having refractive indices varying from 1.60 to 1.72. We have discovered that at the target thickness the difference between the reflectivity signal from the red camera pixel (sensitive predominantly to 580-700 mm) and the reflectivity signal from the blue camera pixel (sensitive predominantly to 420-450 mm) is indicative of the coating thickness, i.e.:

$$t = f([R] - [B]).$$

Figure 3:
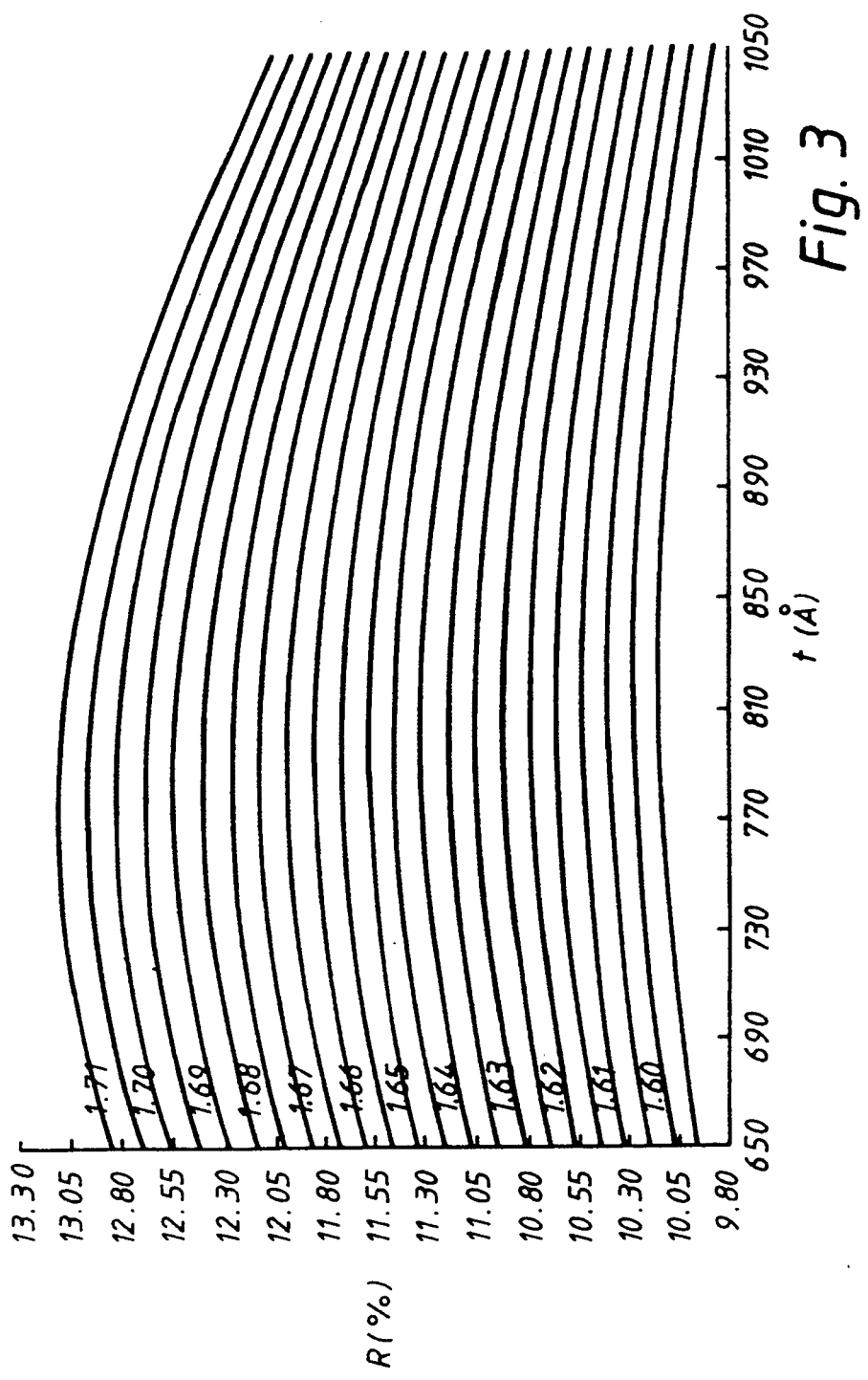
FIG. 3 shows the relationship between reflectivity and coating thickness between 65 and 105 mm, for alumina coatings of various refractive indices.

The refractive index of the coating depends slightly upon the composition, the temperature of the glass and the ambient temperature. At a coating thickness of 75-80 nm the variation of reflectivity with thickness is close to a maximum and therefore changes in thickness result in only minor changes in reflectivity. However, reflectivity changes significantly with the refractive index $\eta_c$ of the coating and therefore one may establish a relationship between reflectivity and refractive index. This relationship is shown in FIG. 3 where average reflectivity R, measured at three discrete monitoring wavelengths, is plotted against thickness t for coatings of refractive index varying from 1.60 to 1.71. Thus, $$\eta_c = f\{([R] + [G] + [B])/3\}$$

In summary therefore the average of the signals generated at the 3 discrete monitoring wavelengths provide information which is proportional to the index of refraction of the coating while the difference between the signals generated at the blue and red wavelengths give information proportional to the thickness of the coating.

The micro-processor may be so programmed as to raise an alarm when the electrical signal, generated from the information indicative of the thickness of the coating, falls outside predetermined threshold values and/or under those conditions to automatically adjust the coating process, for example by changing the reciprocating speed of the spraying head. Similarly, the micro-processor may be so programmed as to raise an alarm when the electrical signal, generated from the information indicative of the refractive index of the coating, falls outside predetermined threshold values and/or under those conditions to automatically adjust the coating process, for example by changing the temperature in the coating station.

EXAMPLE 2

In the case of an absorbing anti-solar coating produced by pyrolysis from acetyl acetonate and comprising 62% CoO, 26% Fe%2O3 and 12% $Cr_2O_3$ with a thickness between 40 and 50 nm, the predominant reflected colour is yellow. An indication of coating optical thickness is obtained from the difference between the electrical signals produced at blue and red wavelengths. In this case however, it is found that the refractive index varies hardly at all once the composition of the coating material is fixed so that geometric thickness is easily controlled.

EXAMPLE 3

In the case of a slightly absorbing anti-solar coating produced by pyrolysis and comprising $TiO_2$ with a thickness of about 80 nm±3 nm, the predominant reflected colour is grey-blue. The difference between the signals at red and blue wavelengths permits monitoring of the optical thickness of this coating.

EXAMPLE 4

In the case of an undercoat comprising $SiO_2$ or $SiO_x$ with a thickness of about 90 nm, the predominant reflected colour is grey. Such a coating may be produced by chemical vapour deposition or alternatively by sputtering, especially radio-frequency sputtering. The reflected colour tends to light blue or to light yellow with changes in coating thickness, but these changes are difficult to detect with the naked eye. In this example, it is preferable to compare the signals produced at green and blue wavelengths to monitor the appearance of this coating.

EXAMPLE 5

In the case of an overcoat comprising $SnO_2$ with a thickness of about 300 nm, coated over an undercoat of alumina with a thickness of 75 nm and applied as indicated in Example 1, there is no predominant reflected colour. If the coating is too thin, a rose-violet reflected colour is obtained. If the coating is too thick, a dull green colour is obtained. The difference between the signals at green and red wavelengths permits monitoring of this coating. The differences between the signals at green and blue wavelengths (or between the signals at red and blue wavelengths) allows the differentiation between two green (or respectively between two red) orders of interference, for example between the 3rd and 4th orders of interference, should the thickness of the coating change substantially.

EXAMPLE 6

A glass substrate has a 25 nm metallic silicon layer deposited thereon by chemical vapour deposition. The normal colour is a metallic grey. When the coating thickness is too great, the colour becomes yellow (and then tends towards the red). The luminous reflection is of the order of 50% and the luminous transmission is about 33%.

The thickness of the coating may be monitored by calculating the difference between the [R] and [B] signals.

EXAMPLE 7

A multi-layer coated substrate glass/TiN/$SnO_2$ (luminous transmission $T_L=35\%$) is produced by magnetron deposition. The product is examined, by reflection from the glass side, using an apparatus according to the invention. The reflected colour is blue. At a constant TiN layer thickness, the difference between the signals at blue and green wavelengths allows for control of the thickness, and the uniformity of thickness, of the upper $SnO_2$ layer in order to ensure a uniform visual aspect of the product when viewed from the glass side. The thickness of the coating of TiN may be previously controlled, according to the invention, by a camera positioned in the deposition apparatus after the deposition of the TiN and before the deposition of the $SnO_2$.

EXAMPLE 8

A highly reflective multi-layer coated substrate glass/stainless steel/TiN (luminous transmission $T_L=8\%$) is produced by magnetron deposition. The product is examined, by reflection from the glass side, using an apparatus according to the invention. The reflected colour is metallic silver and brilliant. At a constant stainless steel layer thickness, the difference between the signals at blue and red wavelengths allows for control of the thickness, and the uniformity of thickness, of the upper TiN layer in order to ensure a uniform visual aspect of the product when viewed from the glass side. The thickness of the coating of stainless steel may be previously controlled, according to the invention, by a camera positioned in the deposition apparatus after the deposition of the stainless steel and before the deposition of the TiN.

What is claimed is:

1. A method of monitoring the thickness and uniformity of thickness of a transparent coating applied to a substrate in sheet form, comprising directing polychromatic light at the coating at a plurality of locations and measuring the intensity of light reflected therefrom, wherein, at each location, the intensity of reflected light is measured at at least two discrete monitoring wavelengths and the measurements are processed to generate an electrical signal which may be compared with one or more predetermined threshold values and with such electrical signals generated at other locations to yield indications of whether the thickness of the coating lies within predetermined tolerance values.

2. The method according to claim 1, wherein the at least two discrete monitoring wavelengths each lie within the range 400 nm to 750 nm and are separated by at least 50 nm.

3. The method according to claim 2, wherein the first discrete monitoring wavelength lies in the range 400 to 480 nm (blue) and the second discrete monitoring wavelength lies in the range 580 to 750 nm (red).

4. The method according to claim 1, wherein measurements are taken at two wavelengths.

5. The method according to claim 1, wherein measurements are taken at three wavelengths.

6. The method according to claim 5, wherein the three measurements are processed to generate an electrical signal indicative of the refractive index of the coating.

7. The method according to claim 5, wherein the first discrete monitoring wavelength lies in the range 400 to 480 nm (blue), the second discrete monitoring wavelength lies in the range 580 to 750 nm (red) and the third discrete monitoring wavelength lies in the range 480 to 580 nm (green).

8. The method according to claim 1, wherein the intensity of reflected light is measured by different light sensitive elements for each discrete monitoring wavelength.

9. The method according to claim 1, wherein the measurement of reflected light is achieved by the use of a charge coupled device (CCD).

10. The method according to claim 9, wherein the charge coupled device is a linear CCD colour camera.

11. The method according to claim 1, wherein the plurality of locations are spaced apart by not more than 50 mm.

12. The method according to claim 11, wherein the plurality of locations are spaced apart by not more than 10 mm.

13. The method according to claim 12, wherein the plurality of locations are spaced apart by not more than 5 mm.

14. The method according to claim 1, wherein the measurements are taken over substantially the whole width of the substrate.

15. The method according to claim 1, wherein the intensity of the polychromatic light directed at the coating is controlled.

16. The method according to claim 1, wherein the measurements are processed to calculate the difference between the intensity of reflected light at two of the discrete monitoring wavelengths.

17. The method according to claim 1, wherein the measurements are made on a moving substrate.

18. The method according to claim 17, wherein the substrate is glass and the measurements are made of a moving glass ribbon or sheets at a location along the production line for the continuous production of coated glass ribbon or sheets.

19. The method according to claim 17, wherein the measurements are made within an annealing lehr on a ribbon of glass obtained by the "float" process.

20. The method according to claim 17, wherein the coating is formed by pyrolysis, and the measurements are taken within 20 m from the down-stream end of the glass coating station.

21. The method according to claim 20, wherein the measurements are taken within 10 m from the down-stream end of the glass coating station.

22. A method of applying a transparent coating to a substrate in sheet form, comprising the steps of:
(a) applying coating material to the substrate;
(b) monitoring the thickness and uniformity of the thickness of the coating by directing polychromatic light at a plurality of locations on the coating, measuring the intensity of light reflected therefrom at each location at at least two discrete monitoring wavelengths and processing the measurements to generate an electrical signal which is compared with one or more predetermined threshold values and with such electrical signals generated at other locations to yield an indication of whether the thickness of the coating lies within predetermined tolerance values; and
(c) adjusting the coating parameters in response to the electrical signal, if necessary.

23. The method according to claim 22, wherein the measurements are made on a moving substrate.

24. The method according to claim 23, wherein the substrate is glass and the measurements are made on a moving glass ribbon or sheets at a location along the production line for the continuous production of coated glass ribbon or sheets.

25. The method according to claim 23, wherein the measurements are made within an annealing lehr on a ribbon of glass obtained by the "float" process.

26. The method according to claim 23, wherein the coating is formed by pyrolysis, and the measurements are taken within 20 m from the down-stream end of the glass coating station.

27. The method according to claim 26, wherein the measurements are taken within 10 m from the down-stream end of the glass coating station.

28. An apparatus for monitoring the thickness and uniformity of the thickness of a transparent coating applied to a substrate, comprising:
(i) a light source for directing polychromatic light at a plurality of locations on the coating;
(ii) means for measuring the intensity of light reflected from the coating at each location at at least two discrete monitoring wavelengths; and
(iii) means for processing the measurements to generate an electrical signal which may be compared with one or more predetermined threshold values and with such electrical signals generated at other locations to lo yield an indication of whether the thickness of the coating lies within predetermined tolerance values.

29. The apparatus according to claim 28, wherein the means for measuring the intensity of light reflected from the coating comprises a linear CCD colour camera.

30. The apparatus according to claim 28, wherein the means for processing the measurement comprises a micro-processor.

31. The apparatus according to claim 28, wherein the light source is an elongate light source having a length equal to at least the width of the coating.

32. The apparatus according to claim 28, further including means for controlling the intensity of polychromatic light directed at the coating, said means including at least one photodetector.

* * * * *